US007927879B2

(12) United States Patent
Sakaguchi et al.

(10) Patent No.: US 7,927,879 B2
(45) Date of Patent: Apr. 19, 2011

(54) ZIRCONIUM CRUCIBLE FOR MELTING ANALYTICAL SAMPLE, METHOD OF PREPARING ANALYTICAL SAMPLE AND METHOD OF ANALYSIS

(75) Inventors: Masahiro Sakaguchi, Ibaraki (JP); Mitsuru Yamaguchi, Ibaraki (JP); Tomio Takahashi, Ibaraki (JP); Kouichi Takemoto, Ibaraki (JP)

(73) Assignee: JX Nippon Mining & Metals Corporation, Tokyo (JP)

( * ) Notice: Subject to any disclaimer, the term of this patent is extended or adjusted under 35 U.S.C. 154(b) by 285 days.

(21) Appl. No.: 12/297,789

(22) PCT Filed: Feb. 20, 2007

(86) PCT No.: PCT/JP2007/053024
§ 371 (c)(1),
(2), (4) Date: Oct. 20, 2008

(87) PCT Pub. No.: WO2007/138768
PCT Pub. Date: Dec. 6, 2007

(65) Prior Publication Data
US 2009/0104082 A1 Apr. 23, 2009

(30) Foreign Application Priority Data
May 26, 2006 (JP) .................................. 2006-146971

(51) Int. Cl.
*G01N 33/20* (2006.01)
(52) U.S. Cl. ................. 436/73; 436/72; 436/77; 436/79; 436/80; 436/82; 436/83; 436/84; 422/401; 422/557; 422/560; 422/908; 75/10.45; 65/32.5; 501/86; 501/102; 501/105; 427/446; 423/76; 423/446; 423/608; 205/192.29; 205/400; 164/497

(58) Field of Classification Search .................. 422/102, 422/908, 401, 557, 560; 436/75–84, 72, 436/73; 75/10.45; 65/32.5; 501/86, 102, 501/105; 427/446; 205/192.29, 400; 164/497
See application file for complete search history.

(56) References Cited

U.S. PATENT DOCUMENTS
3,000,703 A * 9/1961 Brugger ........................ 423/608
(Continued)

FOREIGN PATENT DOCUMENTS
JP 70038971 B * 12/1970
(Continued)

OTHER PUBLICATIONS

Belcher, "Sodium peroxide as a flux in refractory and mineral analysis", Talanta, 1963, vol. 10, pp. 75-81.*

(Continued)

*Primary Examiner* — In Suk Bullock
*Assistant Examiner* — Dennis M White
(74) *Attorney, Agent, or Firm* — Howson & Howson LLP

(57) ABSTRACT

Proposed is a zirconium crucible used for melting an analytical sample in the pretreatment of the analytical sample, wherein the purity of the zirconium crucible is 99.99 wt % or higher. In light of the recent analytical technology demanded of fast and accurate measurement of high purity materials, the present invention provides a zirconium crucible for melting an analytical sample, a method of preparing such analytical sample, and a method of analysis that enables the analysis of high purity materials by inhibiting the inclusion of impurities from the crucible regardless of difference in the analysts and their skill.

7 Claims, 4 Drawing Sheets

U.S. PATENT DOCUMENTS

| | | |
|---|---|---|
| 3,758,662 A | 9/1973 | Tobin et al. |
| 4,946,490 A | 8/1990 | Hall et al. |
| 5,336,378 A | 8/1994 | Nishimura et al. |
| 6,723,672 B1 | 4/2004 | Stuart et al. |
| 2005/0221088 A1 | 10/2005 | Celik et al. |
| 2007/0051440 A1 | 3/2007 | Eucken |
| 2009/0053112 A1 | 2/2009 | Shindo et al. |
| 2010/0167407 A1 | 7/2010 | Sakaguchi et al. |

FOREIGN PATENT DOCUMENTS

| | | |
|---|---|---|
| JP | 10-132801 A | 5/1998 |
| JP | 2004-069413 A | 3/2004 |

OTHER PUBLICATIONS esp@cenet database, One Page English Abstract of JP 10-038773 A, Feb. 13, 1998.

esp@cenet database, One Page English Abstract of JP 02-172540 A, Jul. 4, 1990.

esp@cenet database, One Page English Abstract of JP 58-048854 A, Mar. 22, 1983.

esp@cenet database, One Page English Abstract of JP 2005-114505 A, Apr. 28, 2005.

Co-Pending U.S. Appl. No. 12/278,889 which is the national phase of International Application No. PCT/2007/052711 filed Feb. 15, 2007.

Co-Pending U.S. Appl. No. 12/188,446, filed Aug. 8, 2008.

U.S. Office Action dated Aug. 17, 2010 issued in co-pending U.S. Appl. No. 12/188,446.

U.S. Office Action dated Aug. 13, 2010 issued in co-pending U.S. Appl. No. 12/278,889.

* cited by examiner

ZIRCONIUM CRUCIBLE FOR MELTING ANALYTICAL SAMPLE, METHOD OF PREPARING ANALYTICAL SAMPLE AND METHOD OF ANALYSIS

BACKGROUND OF THE INVENTION

The present invention relates to a zirconium crucible for melting an analytical sample, a method of preparing such analytical sample, and a method of analysis that enables the analysis of high purity samples by inhibiting the inclusion of impurities from the crucible and regardless of difference in the analysts and their skill.

In recent years, demands for measuring high purity materials quickly and accurately are on the rise. With the increase of such demands, there is a problem in that the measurement result will differ depending on skill of the analysts, and reanalysis must be performed from time to time in order to confirm the reliability of the initial analysis.

A sample for analysis is generally prepared by melting the sample with a flux. The process of melting the sample with a flux is usually based on a melting method such as carbonate (alkali) fusion, alkali hydroxide fusion, sodium peroxide fusion, or sodium hydrogensulfate fusion.

Among the above, sodium peroxide has strong oxidizing power, and is a favorable flux. Although an iron or nickel crucible is often used as the melting crucible in the foregoing case, it is necessary to take into consideration that the crucible will be severely affected.

Although the ratio of mixing this sodium peroxide fusion will differ depending on the nature of the sample, generally, 5 to 10 parts in weight of sodium peroxide is used in relation to the sample weight (Non-Patent Document 1). In addition, the heating temperature must also be changed according to the sample, and this is decided entirely by experience.

Conventionally, although the quantitative value was sought by subtracting the blank of the crucible, variation in the blank depends largely on the skill of the analyst. Further, since a conventional zirconium crucible has a purity level of 99 wt % (2N), impurities from the crucible would get mixed in, the lower limit of determination would become high as a result of the mixture of such impurities, and this was insufficient for the analysis of recent high purity samples.

Although there are not many Patent Documents that describe an analytical means to handle the foregoing high purity materials, to introduce some materials that may be of reference, for instance, there is technology that relates to the method of adjusting a sample for performing qualitative and quantitative analysis of such sample, whereby the sample is placed on a metal foil and subject to thermolysis together with such metal foil, and further made into a solution (Patent Document 1). Nevertheless, this is an extremely atypical type of method, and lacks versatility.

Further, a chemical analysis crucible composed from Pt alloy or Pd alloy in which 5 to 90 wt % of Pd is added to Pt that uses an alkali flux to perform chemical analysis of ores is disclosed (Patent Document 2). Nevertheless, this technology is subject to the use of expensive crucible materials, and there is a problem in that it is impractical since an alloy will be formed depending on the sample elements.

In addition, a method of analyzing the rhodium content in a film by heating and melting a rhodium-ruthenium alloy plating film in a nickel crucible with sodium peroxide or potassium peroxide is disclosed (Patent Document 3). Nevertheless, Patent Document 3 does not in any way disclose the purity of the crucible. Thus, it is strongly assumed that the crucible of Patent Document 3 has a conventional purity level (2N level). Thus, there is a problem in that the lower limit of determination is high due to the inclusion of impurities, and high precision analysis cannot be performed.

[Non-Patent Document 1] "Analysis" Introductory Course, Issued in Oct. 1979, "Reagent Used in Dissolution" Pages 648 to 655

[Patent Document 1] Japanese Patent Laid-Open Publication No. H10-38773

[Patent Document 2] Japanese Patent Laid-Open Publication No. H2-172540

[Patent Document 3] Japanese Patent Laid-Open Publication No. S58-48854

SUMMARY OF THE INVENTION

In light of the recent analytical technology demanded of fast and accurate measurement of high purity materials, an object of the present invention is to provide a zirconium crucible for melting an analytical sample, a method of preparing such analytical sample, and a method of analysis that enables the analysis of high purity materials by inhibiting the inclusion of impurities from the crucible regardless of difference in the analysts and their skill.

In order to achieve the foregoing object, the present invention provides:

1) A zirconium crucible used for melting an analytical sample in the pretreatment of the analytical sample, wherein the purity of the zirconium crucible is 99.99 wt % or higher.

2) The zirconium crucible used for melting according to paragraph 1) above which uses a basic flux comprising one or more types of alkali chemicals selected from $Na_2CO_3$, $K_2CO_3$, $H_3BO_3$, NaOH, KOH, $Na_2B_2O_7$, $Li_2B_2O_7$ and the like, and/or a basic flux added with one or more types of oxidizing agents selected from $Na_2O$, $Na_2O_2$, $K_2O$, $K_2O_2$, $KNO_3$, $KClO_3$ and the like, or one or more types of acid flux selected from $Na_2S_2O_7$, $K_2S_2O_7$, $NaHSO_4$ and the like to melt the analytical sample. The list of fluxes is in Table 1. In particular, sodium peroxide is a favorable flux.

Incidentally, although Table 1 shows the oxidizing agent to be a basic flux to be used in combination with alkali, as described above, this oxidizing agent can also be used as an independent flux.

3) A method of preparing an analytical sample using a high purity zirconium crucible, including a step of preliminarily melting a sample in a zirconium crucible having a purity of 99.99 wt % or higher to obtain the analytical sample.

4) The method of preparing an analytical sample according to paragraph 3) above, further including a step of measuring and placing a sample in the crucible, and melting the sample using a basic flux comprising one or more types of alkali chemicals selected from $Na_2CO_3$, $K_2CO_3$, $H_3BO_3$, NaOH, KOH, $Na_2B_2O_7$, $Li_2B_2O_7$ and the like, and/or a basic flux added with one or more types of oxidizing agents selected from $Na_2O$, $Na_2O_2$, $K_2O$, $K_2O_2$, $KNO_3$, $KClO_3$ and the like, or one or more types of acid flux selected from $Na_2S_2O_7$, $K_2S_2O_7$, $NaHSO_4$ and the like to obtain the analytical sample. In particular, sodium peroxide is a favorable flux.

5) A method of analysis, including the steps of melting a sample using a zirconium crucible used for melting having a purity of 99.99 wt % or higher, and analyzing the result to obtain an analytical result in which the respective lower limit of determination of Mn, Al, Si, Mg, Co, Ti, Cu, Mo, Fe, Cr, W, Pb, and Ni are 10 wtppm or less.

TABLE 1

| Basic Flux | | |
|---|---|---|
| Alkali | Oxidizing Agents | Acid Flux |
| $Na_2CO_3$, $K_2CO_3$, $H_3BO_3$, NaOH, KOH, $Na_2B_2O_7$, $Li_2B_2O_7$, etc. | $Na_2O$, $Na_2O_2$, $K_2O$, $K_2O_2$, $KNO_3$, $KClO_3$, etc. | $Na_2S_2O_7$, $K_2S_2O_7$, $NaHSO_4$, etc. |

As a result of using the high purity zirconium crucible in which the purity of the zirconium crucible is 99.99 wt % or higher, the present invention yields a superior effect in that it is able to inhibit the inclusion of impurities from the crucible and perform analysis with a lower limit of determination regardless of the difference in analysts and their skill, to save the labor time and mitigate the amount of reagent to be used, and, therefore, the present invention is able to meet the demands of recent analytical technology which require fast and accurate measurement of high purity materials.

DETAILED DESCRIPTION OF THE INVENTION

Figure 2:
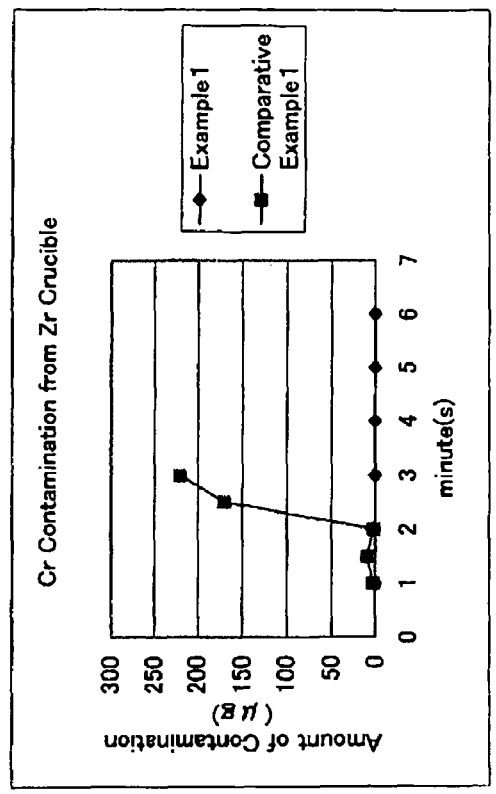
FIG. 2 is a diagram showing the contamination level of Cr from the zirconium crucible.
Figure 1:
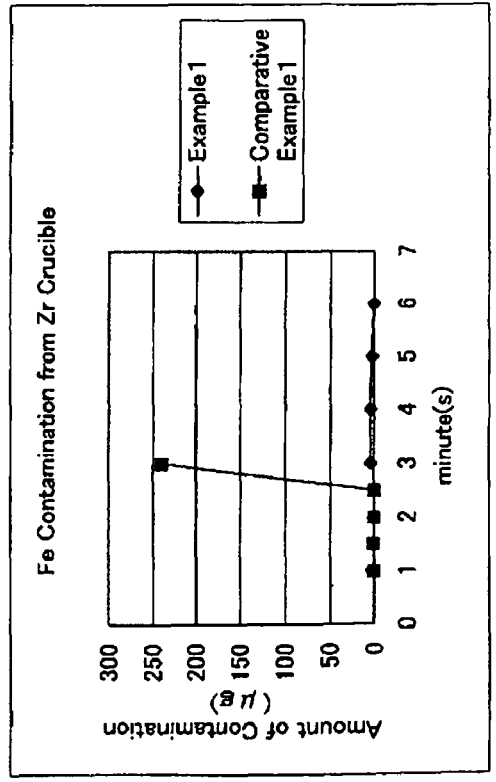
FIG. 1 is a diagram showing the contamination level of Fe from the zirconium crucible.
Figure 4:
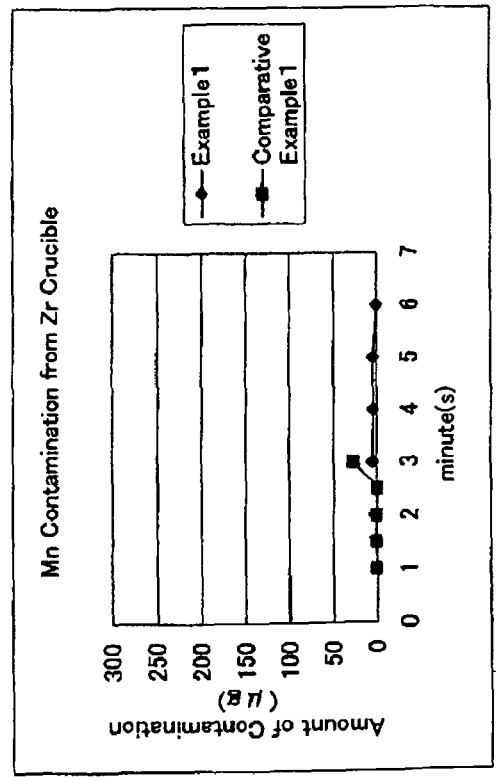
FIG. 4 is a diagram showing the contamination level of Al from the zirconium crucible.
Figure 3:
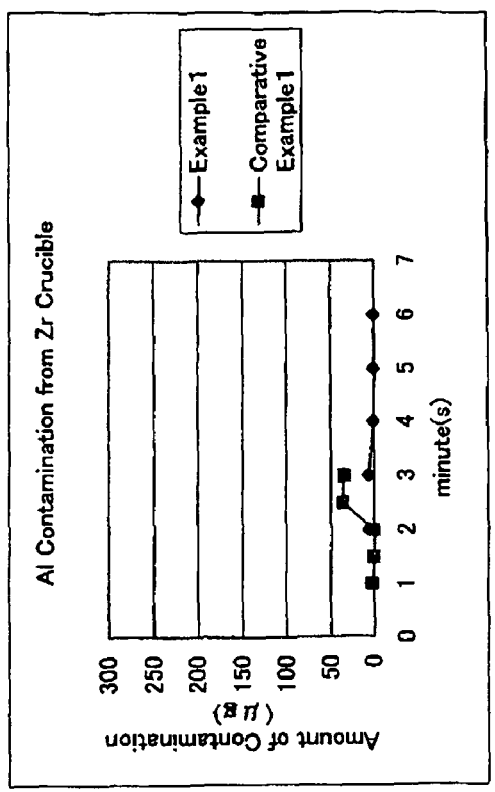
FIG. 3 is a diagram showing the contamination level of Mn from the zirconium crucible.
Figure 6:
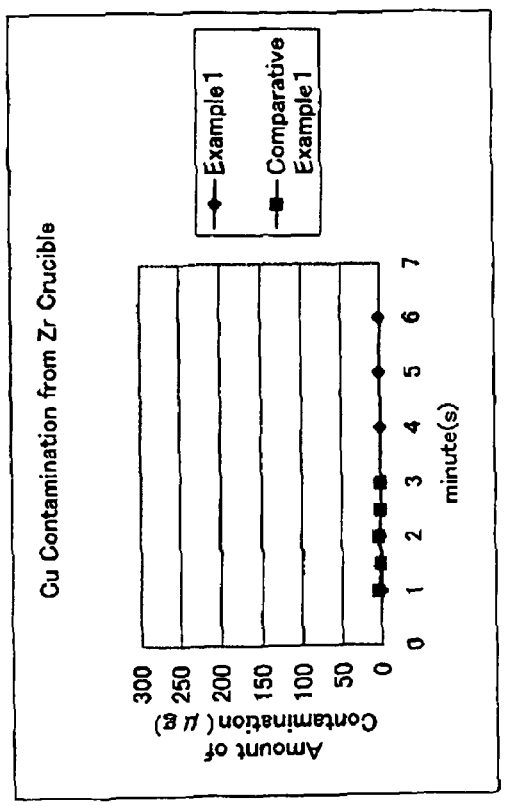
FIG. 6 is a diagram showing the contamination level of Cu from the zirconium crucible.
Figure 5:
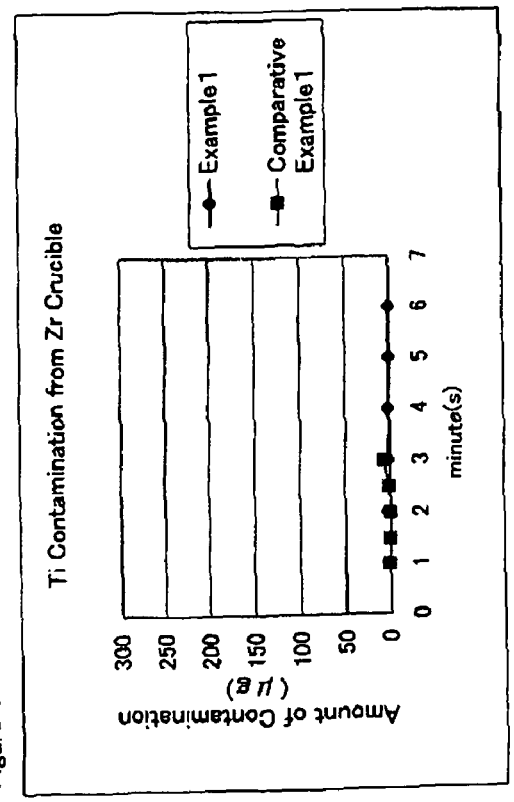
FIG. 5 is a diagram showing the contamination level of Ti from the zirconium crucible.

As the zirconium crucible used for melting an analytical sample in the pretreatment of such analytical sample according to the present invention, a zirconium crucible having a purity of 99.99 wt % or higher is used.

The general procedures for performing the analysis of the present invention are as follows.

(1) Place the sample in the zirconium crucible.
(2) Add a flux, such as an alkali flux, to the crucible.
(3) Heat the crucible with a burner and melt the flux and sample.
(4) Transfer the sample to a PTFE beaker or the like.
(5) Add acid and the like.
(6) Heat the beaker and dissolve the sample.
(7) Transfer the sample to a volumetric flask.
(8) Add water until the liquid measure becomes a prescribed value.
(9) Measure the result with an ICP-AES or the like.

As a result of using the foregoing zirconium crucible for melting of a purity of 99.99 wt % or higher to melt the sample, and thereafter analyzing such sample, the present invention yields a superior effect of being able to obtain an analytical result where the respective lower limit of determination of Mn, Al, Si, Mg, Co, Ti, Cu, Mo, Fe, Cr, W, Pb, and Ni are 10 wtppm or less.

A conventional zirconium crucible contains hundreds to thousands wtppm of Fe. Thus, there is a problem in that the Fe contamination from the zirconium crucible during the analysis will be high. In addition, a conventional zirconium crucible also entails a problem of Cr elution.

Thus, it is necessary to control the heating time and the like to prevent Fe and Cr in the crucible from eluting, and advanced techniques and experience were required for analysis since the melting status at such time must be confirmed visually.

Nevertheless, as a result of employing the high purity zirconium crucible of the present invention which has low Fe and Cr content, there is an advantage in that even non-experienced analysts can conduct the analysis easily since the elution of Fe and Cr will be minimal even when the melting conditions are controlled roughly.

EXAMPLES

The present invention is now explained based on the Example and Comparative Example. This Example merely illustrates a preferred example, and the present invention shall in no way be limited thereby. In other words, other embodiments and modes shall be included in this invention.

Example 1

The Example of the present invention used a high purity zirconium crucible (high purity product) having a purity of 99.99 wt %, and quantitative determination of impurities (Fe, Cr, etc.) in $ZrO_2$ as the subject of quantitative determination was performed. The analytical conditions and analytical results were as follows.

A sample in the amount of 0.5 g was placed in the foregoing high purity zirconium crucible, 5 g of sodium peroxide was used as the flux, the sample was heated with a burner, and subsequently added with 20 ml of hydrochloric acid (HCl) and 50 ml of ultrapure water.

The sample was transferred to a 300 ml teflon beaker, and heated and dissolved. After dissolution, the total volume was placed in a 250 ml flask, ultrapure water was added thereto, and the liquid measure was prescribed. The obtained sample was measured with an ICP-AES. The blank is a result of 6 tests. The measurement results of primary impurities (Fe, Cr, Mn, Al, Ti, Cu) that eluted from the crucible are shown in FIG. 1 to FIG. 6 respectively.

As shown in FIG. 1 to FIG. 6, in comparison to the Comparative Example (background art) shown below, it is easy to understand that, by using the high purity zirconium crucible of the present invention, the elution hardly changes over time, and the amount thereof is also minimal. Like this, it is possible to inhibit the elution of impurities such as Fe, Cr, Mn, Al, Ti, and Cu to a minimum, and a superior effect was yielded in that high precision analysis could be performed. In particular, it is evident that the contamination of Fe and Cr from the zirconium crucible can be effectively inhibited.

Although the impurities of Mn, Al, Ti, and Cu are not that different in comparison to the Comparative Example described later, since the absolute amount of contamination from the Zr crucible is small originally, there will be no significant difference. Nevertheless, in either case, in comparison to the Comparative Example, it is evident that the contamination from the zirconium crucible is minimal.

Upon checking the lower limit of determination of Fe (defined as 10 times the standard deviation ($\sigma$) based on the measurement of 6 blank samples), the lower limit of determination of Fe in the Example was 10 wtppm.

Thus, as a result of success in reducing the lower limit of determination of Fe significantly, a superior yield of applying the present invention to the analysis of persistent impurities was also obtained.

Comparative Example 1

In Comparative Example 1, a zirconium crucible having a purity of 99 wt % was used. As with Example 1, quantitative determination of impurities (Fe, Cr, etc.) in $ZrO_2$ as the subject of quantitative determination was performed. Sodium peroxide was used as the flux as in Example 1. The blank is a result of 6 tests. The analytical results are also shown FIG. 1 to FIG. 6 in comparison to Example 1. The analytical conditions and analytical results were as follows.

As shown in FIG. 1 to FIG. 6, Comparative Example 1 (background art) resulted in significant elution of impurities. This amount increased considerably 2 to 3 minutes later. In particular, the increase of Fe and Cr is significant, and Mn and Al also increased. The increase of such impurities entails a problem in that high precision analysis cannot be performed.

Like this, with the conventional zirconium crucible shown in Comparative Example 1, since the purity was low at a level of 2N, the impurity content was high, and, when acid was used to analyze the impurities in the persistent sample, a problem arose in that the contamination from the crucible would increase.

The lower limit of determination was defined as 10 times the standard deviation ($\sigma$) based on the measurement of 6 blank samples, and the lower limit of determination of the elution of Fe from the zirconium crucible of Comparative Example 1 was checked in comparison to the zirconium crucible of Example 1 of the present invention. As a result, the zirconium crucible of Comparative Example 1 had a lower limit of determination of 50 wtppm and showed an inferior result.

As described above, there is a significant difference in the lower limit of determination in the Example and the Comparative Example, and it has been confirmed that the lower limit of determination of the present invention showed considerable improvement.

Figure 7:
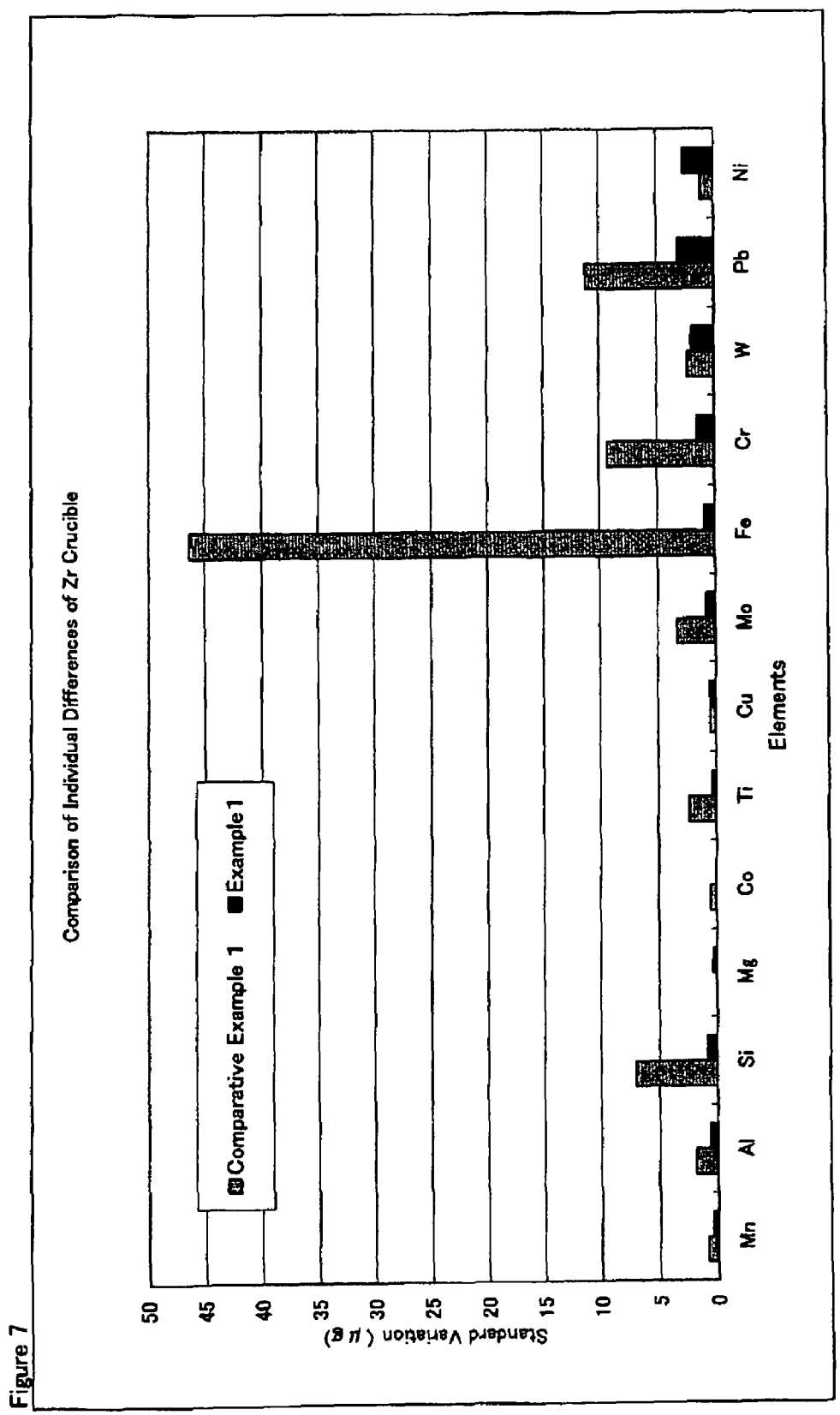
FIG. 7 is a diagram showing the variation in the impurity elution pertaining to the individual difference of the zirconium crucible.

Next, variation in the elution of impurities accompanying the individual differences of the zirconium crucible is shown in Table 2 and FIG. 7. As shown in Table 2 and FIG. 7, although the variation among the individual samples is significant in Comparative Example 1, and variation among individual samples in Example 1 shows a sufficiently small standard deviation. If the variation among individual samples is small, this yields an effect of improving the analytical precision and further reduces the lower limit of determination.

TABLE 2

Standard Deviation among Individual Samples (μg)

| | Mn | Al | Si | Mg | Co | Ti | Cu | Mo | Fe | Cr | W | Pb | Ni |
|---|---|---|---|---|---|---|---|---|---|---|---|---|---|
| Comparative Example 1 | 0.8 | 1.8 | 7.0 | 0.03 | 0.6 | 2 | 0.5 | 3.3 | 46 | 9 | 2.4 | 11 | 1.1 |
| Example 1 | 0.4 | 0.7 | 0.9 | 0.3 | 0.1 | 0.4 | 0.5 | 0.8 | 0.88 | 2 | 2.0 | 3 | 2.7 |

Although the sample was dissolved using sodium peroxide in the foregoing Example, it should be easily understood that the lower limit of determination could also be reduced when using other fluxes, such as a basic flux comprising one or more types of alkali chemicals selected from $Na_2CO_3$, $K_2CO_3$, $H_3BO_3$, NaOH, KOH, $Na_2B_2O_7$, $Li_2B_2O_7$ and the like, and/or a basic flux added with one or more types of oxidizing agents selected from $Na_2O$, $Na_2O_2$, $K_2O$, $K_2O_2$, $KNO_3$, $KClO_3$ and the like, or one or more types of acid flux selected from $Na_2S_2O_7$, $K_2S_2O_7$, $NaHSO_4$ and the like.

As a result of using the high purity zirconium crucible of the present invention in which the purity of the zirconium crucible is 99.99 wt % or higher, it is possible to perform high purity analysis by inhibiting the inclusion of impurities from the crucible regardless of the difference in the analysts and their skill. Since the present invention additionally yields a superior effect of saving the labor time and mitigating the amount of reagent to be used, it is possible to meet the demands of recent analytical technology which require fast and accurate measurement of high purity materials.

The invention claimed is:

1. A zirconium crucible utilized for melting an analytical sample in the pretreatment of the analytical sample, wherein the zirconium crucible consists of zirconium metal having a purity of 99.99 wt % or higher.

2. The zirconium crucible utilized for melting an analytical sample according to claim 1, wherein the melting of the analytical sample is performed by using a basic flux comprising one or more types of alkali chemicals selected from $Na_2CO_3$, $K_2CO_3$, $H_3BO_3$, NaOH, KOH, $Na_2B_2O_7$, and $Li_2B_2O_7$, or said basic flux added with one or more types of oxidizing agents selected from $Na_2O$, $Na_2O_2$, $K_2O$, $K_2O_2$, $KNO_3$, and $KClO_3$, or one or more types of acid flux selected from $Na_2S_2O_7$, $K_2S_2O_7$, and $NaHSO_4$.

3. A zirconium crucible according to claim 1, wherein said zirconium crucible provides lower limits of quantification for each of Mn, Al, Si, Mg, Co, Ti, Cu, Mo, Fe, Cr, W, Pb, and Ni of 10 wtppm or less.

4. A method of treating an analytical sample using a high purity zirconium crucible, including a step of preliminarily melting the analytical sample in a zirconium crucible to obtain the analytical sample, the zirconium crucible consisting of zirconium metal having a purity of 99.99 wt % or higher.

5. The method of treating an analytical sample according to claim 4, further including steps of weighing and placing the analytical sample in the crucible, and during said preliminary melting step, melting the analytical sample using a basic flux comprising one or more types of alkali chemicals selected from $Na_2CO_3$, $K_2CO_3$, $H_3BO_3$, NaOH, KOH, $Na_2B_2O_7$, and $Li_2B_2O_7$, or said basic flux added with one or more types of oxidizing agents selected from $Na_2O$, $Na_2O_2$, $K_2O$, $K_2O_2$, $KNO_3$, and $KClO_3$, or one or more types of acid flux selected from $Na_2S_2O_7$, $K_2S_2O_7$, and $NaHSO_4$.

6. A method according to claim 4, further comprising the step of analyzing the analytical sample as melted during said preliminary melting step with lower limits of quantification for each of Mn, Al, Si, Mg, Co, Ti, Cu, Mo, Fe, Cr, W, Pb, and Ni of 10 wtppm or less.

7. A method of analysis, including the steps of melting an analytical sample by using a zirconium crucible consisting of zirconium metal having a purity of 99.99 wt % or higher, and performing analyses with the analytical sample melted during said melting step to obtain analytical results, in which lower limits of quantification for each of Mn, Al, Si, Mg, Co, Ti, Cu, Mo, Fe, Cr, W, Pb, and Ni is 10 wtppm or less.

\* \* \* \* \*

UNITED STATES PATENT AND TRADEMARK OFFICE
CERTIFICATE OF CORRECTION

| | | |
|---|---|---|
| PATENT NO. | : 7,927,879 B2 | Page 1 of 1 |
| APPLICATION NO. | : 12/297789 | |
| DATED | : April 19, 2011 | |
| INVENTOR(S) | : M. Sakaguchi et al. | |

It is certified that error appears in the above-identified patent and that said Letters Patent is hereby corrected as shown below:

Column 6, line 7 -- "$K2O21$" -- should read -- $K2O2$ --

Signed and Sealed this
Fifth Day of July, 2011

David J. Kappos
*Director of the United States Patent and Trademark Office*